United States Patent [19]

Shaw

[11] Patent Number: 5,120,300

[45] Date of Patent: Jun. 9, 1992

[54] COMPRESSION BAND FOR QUICK APPLICATION

[76] Inventor: Frank D. Shaw, 18 Oakwood La., Rumson, N.J. 07760

[21] Appl. No.: 614,260

[22] Filed: Nov. 16, 1990

[51] Int. Cl.$^5$ .................. A61F 13/00; A44B 18/00
[52] U.S. Cl. ........................... 602/61; 602/64; 602/75; 128/876; 128/DIG. 15; 606/203; 24/442
[58] Field of Search ............... 128/78, 876, 156, 165, 128/166, 169, 171, DIG. 15; 24/442, 306; 606/203

[56] References Cited

U.S. PATENT DOCUMENTS

| | | | |
|---|---|---|---|
| 3,086,529 | 4/1963 | Munz et al. | 128/171 |
| 3,182,338 | 5/1965 | Shirrod | 128/876 |
| 4,215,687 | 8/1980 | Shaw | 128/169 |
| 4,273,130 | 6/1981 | Simpson | 128/171 X |

Primary Examiner—Richard J. Apley
Assistant Examiner—Linda C. M. Dvorak
Attorney, Agent, or Firm—Brumbaugh, Graves, Donohue & Raymond

[57] ABSTRACT

A compression band including male and female connectors and a length of compression band integrally connected to one of the connectors so that the compression band can be quickly and easily applied and removed by preassembling the male and female connectors so that the preassembled compression band can be encompassed about a body, limb or object and fastened in place by adhering inner fastening surfaces of the preassembled connectors to the outer fastening surface of the compression band. The desired tension can then be applied by separating free ends of the connectors, tensioning the band and reapplying the free ends against the outer fastening surface of the band.

7 Claims, 1 Drawing Sheet

COMPRESSION BAND FOR QUICK APPLICATION

BACKGROUND OF THE INVENTION

This invention relates to a compression band for quick and easy application to and quick and easy removal from a body, limb or other object in which, after quick application, the compression band can be tightened to apply the desired compression.

Therapeutic compression bands of this general type are described in my U.S. Pat. No. 4,215,687 which description is incorporated herein.

The compression bands described in my U.S. Pat. No. 4,215,687 are integral VELCRO bands having male and female connectors at opposite ends. These integral compression bands are available in different lengths, depending on the girth to be encompassed, and the selected length is generally longer than necessary. In use, intermediate lengths of the band are usually removed and spliced to reduce the length of the band to the desired length and also to permit the spliced bands to be angularly adjusted to conform the band to the shape of the body or limb so that the band will apply uniform compression throughout its width, that is to say, from the upper edge to the lower edge thereof. When the band has been properly spliced, the band is tightened and anchored by the interconnection of the male and female connecting ends.

SUMMARY OF THE INVENTION

The invention relates to a novel compression band which includes male and female connectors in which one of the connectors is formed integrally at the end of an extended length of a compression band having an outer fastening surface. By preassembling the male and female connectors, the compression band of the present invention can be quickly applied to a body, limb or object by holding the end of the compression band against the surface to which it is to be applied, encircling the band around the body, limb or object and then pressing inner fastening surfaces of the preassembled connectors to the outer fastening surface of the compression band. The compression band thus having been quickly applied to the body, limb or object to be encompassed, the proper compression can now be applied by separating inner fastening surfaces of opposite ends of the male and female connectors from the outer fastening surface of the compression band and pulling the ends to apply the desired compression. The ends of the male and female connectors are then pressed against the outer fastening surface of the compression band to secure the compression band and to maintain the desired compression.

DESCRIPTION OF THE DRAWINGS

For an understanding of the present invention, reference should be made to the detailed description which follows and to the accompanying drawings in which.

DETAILED DESCRIPTION OF THE INVENTION

Figure 1:
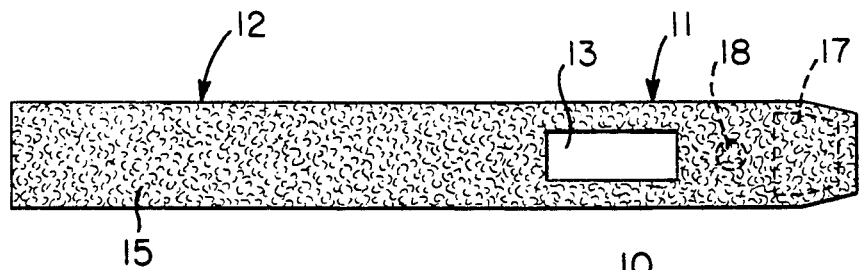
FIG. 1 shows one surface of a female connector integrally formed at the end of a length of a compression band.
Figure 2:
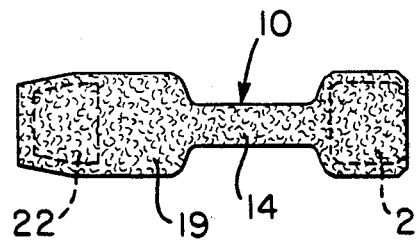
FIG. 2 shows a surface of a male connector.

FIGS. 1 and 2 show male and female connectors 10 and 11, respectively. The female connector is integrally formed with a length of compression band 12. The compression band 12 is shown integrally formed with the female connector 11, but can instead be formed integrally with a male connector 10.

The female connector 11 includes a band having an elongated opening 13 therein. The male connector includes a band having a narrow strip 14 intermediate its ends.

The compression band 12 and the female connector 11 have a continuous VELCRO loop fastening outer surface 15 and an inner smooth surface 16. The smooth surface of the female connector 11 has a pair of VELCRO hook fastening surfaces 17, 18 intermediate the elongated opening 13 and the end of the female connector.

The male connector 10 has an outer VELCRO loop fastening surface 19 and an inner smooth surface 20 having VELCRO hook fastening surfaces 21 at one end and 22 at the other end.

Figure 3:
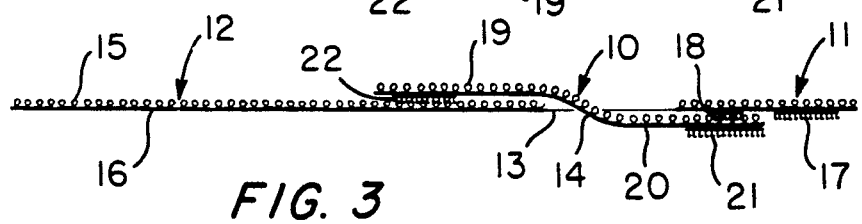
FIG. 3 is a section view showing the male and female connectors preassembled for quick application of the band.

The male and female connectors are preassembled in the manner illustrated in FIG. 3. The outer loop fastening surface of the male connector is pressed against the hook surface 18 of the female connector, the opposite end of the male connector is threaded through the elongated opening 13 in the female connector, inserting the narrow elongated strip 14 of the male connector within the elongated opening 13, and the hook fastening surface 22 at the other end of the male connector is pressed against the outer loop fastening surface 15 of the compression band. The compression band is now ready for quick application to the body, limb or object which it is intended to encompass.

Figure 4:
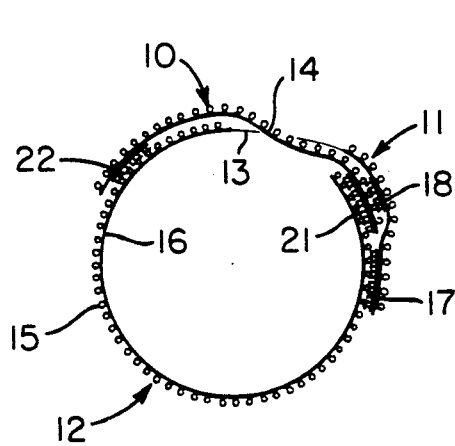
FIG. 4 shows the preassembled compression band applied to a body, limb or object.

The preassembled compression band is applied to the body, limb or object to be encompassed by holding the smooth surface of the free end of the compression band 12 against the body, wrapping the band around the surface to be compressed and then pressing the hook fastening surfaces 17 of the female connector and 21 of the male connector against the outer loop fastening surface 15 of the compression band. The compression band, although not necessarily properly tensioned to apply the desired compression, is thus quickly applied in the manner shown in FIG. 4.

Figure 5:
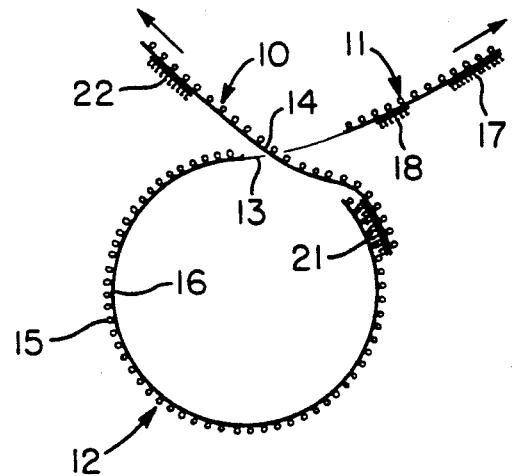
FIG. 5 is a view similar to FIG. 4 showing the ends of the male and female connectors separated from the outer fastening surface of the compression band for tensioning the compression band after it has been applied.

The compression band is properly tensioned by lifting the opposite ends of the male and female connectors as shown in FIG. 5, to separate the inner hook fastening surface 22 of the male connector from the outer loop fastening surface 15 of the compression band and lifting the hook fastening surfaces 17, 18 of the female connector away from the outer loop fastening surfaces 15 of the compression band and 19 of the male connector. By the force applied to the lifted ends, the movement of the narrow elongated strip 14 of the male connector within and relative to the elongated opening 13 of the female connector permits increase or decrease in the tension of the compression band to apply the desired compression. When the desired compression has been achieved, the lifted ends of the male and female connectors are pressed against the outer loop fastening surface 15 of the compression band to maintain desired compression. After application, the overall length of the compression band may be either left in place or cut off to a desired length at a convenient time.

Figure 6:
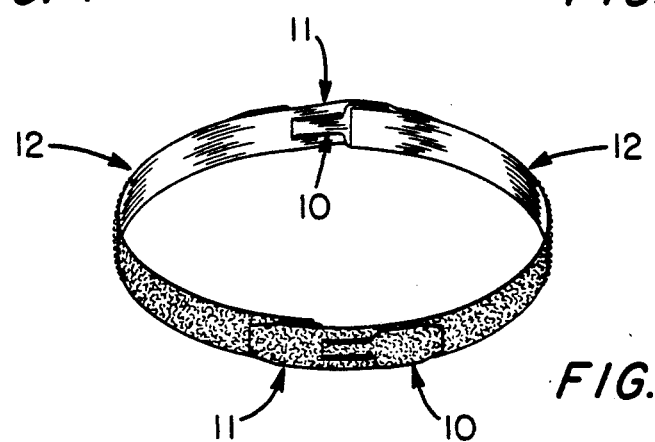
FIG. 6 is a perspective view showing series connected compression bands of the present invention.

Two or more bands may be employed on the body in edge-to-edge parallel relationship to apply compression to larger areas of the body, as described in my U.S. Pat. No. 4,215,687. These parallel compression bands may be held in parallel relationship by the application of perpendicular bands having VELCRO hook fastening surfaces applied to the outer VELCRO loop fastening surfaces of the parallel compression bands. Also, as shown in FIG. 6, two or more bands may be connected in series to provide compression adjustment and/or openings for inspection and treatment at selected areas covered by the band.

Uniform compression on areas covered by a band is accomplished by keeping both edges of the band in contact with the encompassed areas while applying the band and engaging the hook tape ends of the male and female connectors to the outer loop surface of the band. This is a simpler and faster means of obtaining uniform pressure application than can be achieved by the compression band disclosed in my U.S. Pat. No. 4,215,687.

The device of the present invention combines simplicity with the rapidity of application, removal and compression adjustment which is especially important in trauma, sclerosing and anti-embolism leg compression applications.

The compression bands of the present invention also have application in compression therapy of venous and lymphatic insufficiency consequences which include leg ulcers, lymphedema, postural hypotension, cellulitis, postphlebetic syndrome, leg edema, puritis and dermatitis. Compression bands of the present invention may also be used in bandaging and to hold bandages, such as the Montgomery bandage, in place without the use of or minimal use of adhesive tapes which can cause trauma and allergic reactions of the skin. They can also be used for or in conjunction with orthopedic devices, for example, orthopedic devices used for fractures, sprains, containment, support and compression.

The fastening surface 21 of the male component is preferably a high peel strength mushroom hook fastening surface located at the extreme end of the male component to prevent accidental disengagement during the tensioning of the band shown in FIG. 5. The hook fastening surface 18 of the female connector holds the loop fastening surface 19 in place to prevent it from separating from and hanging free in preassembled condition. The fastening surface 18 is preferably a low peel strength so as not to cause disengagement of the high peel strength fastening surface 21 from the loop fastening surface 15 of the compression band during tensioning.

The invention has been shown in preferred forms and by way of example and modifications and variations are possible within the spirit of the invention. For example, as described above, the male connector can be integrally formed with the compression band and the female connector may be used as a separate component for preassembly with the male connector. The invention, therefore, is not intended to be limited to any specified form or embodiment, except insofar as such limitations are expressly set forth in the claims.

I claim:

1. A compression band for quick application comprising male and female connectors, the female connector including a band having an opening therein and the male connector including a band having a narrow strip intermediate its ends for insertion through the opening in the female connector to secure the compression band about a surface to be encompassed, a length of compression band integrally formed with one of the connectors and having an outer fastening surface, the connector integrally formed with the compression band having an inner fastening surface near its end for adherence to the outer fastening surface of the compression band, the other connector having inner fastening surfaces at both ends for adherence to the outer fastening surface of the compression band and having an outer fastening surface for adherence to at least a portion of the inner fastening surface of the connector integrally connected with the compression band.

2. A compression band as set forth in claim 1 in which the male and female connectors are preassembled so that the compression band can be quickly and easily applied to and quickly and easily removed from the body by encircling the compression band about the body and adhering the inner fastening surfaces of the preassembled connectors to the outer fastening surface of the compression band, the tightening of the compression band being accomplished by separating the ends of the engaged connectors and pulling them to apply the desired tension and then adhering them by pressing the ends against the outer fastening surface of the compression band to maintain the tension.

3. A method of applying the compression band set forth in claim 1 on a part of the body or other object comprising preassembling the male and female connectors by inserting the narrow strip of the male connector through the opening in the female connector, adhering one of the inner fastening surfaces of the said other connector to the outer fastening surface of the compression band and adhering the outer fastening surface of said other connector to the inner surface of the connector integrally connected with the compression band.

4. A method as set forth in claim 3 including the steps of holding the free end of the connector band against the body and encircling the band about the body, adhering the inner fastening surfaces of both connectors to the outer fastening surface of the compression band, separating the inner fastening surfaces of both connectors from the outer fastening surface of the compression band, pulling the connectors to tension the compression band and adhering the inner fastening surfaces of the connectors to the outer fastening surface of the compression band to retain the tension.

5. A method as set forth in claim 3 which includes preassembling at least two compression bands and connecting them in series.

6. A compression band as set forth in claim 1 in which the fastening surfaces between the said other connector and the band provide stronger adherence than the fastening surfaces between the two connectors so that the preassembled connectors can be more easily separated for tensioning the compression band without disconnecting the said other connector from the compression band.

7. A compression band as set forth in claim 1 in which the fastening surfaces are hook-type and loop-type fasteners, the compression band has a smooth surface on its inner side, the fasteners of the outer surfaces of the compression band and of the male and female connectors are of one type and the fasteners of the inner surfaces of the male and female connectors are of the other type.

* * * * *